United States Patent
Ohama (10) Patent No.: US 9,170,206 B2
(45) Date of Patent: Oct. 27, 2015

(54) INSPECTION APPARATUS FOR SHEET

(71) Applicant: KOMORI CORPORATION, Tokyo (JP)

(72) Inventor: Kentaro Ohama, Tsukuba (JP)

(73) Assignee: KOMORI CORPORATION, Tokyo (JP)

( * ) Notice: Subject to any disclaimer, the term of this patent is extended or adjusted under 35 U.S.C. 154(b) by 282 days.

(21) Appl. No.: 13/946,102

(22) Filed: Jul. 19, 2013

(65) Prior Publication Data
US 2014/0022379 A1 Jan. 23, 2014

(30) Foreign Application Priority Data

Jul. 20, 2012 (JP) ................................. 2012-161219

(51) Int. Cl.
| | | |
|---|---|---|
| *H04N 7/18* | (2006.01) | |
| *G01N 21/86* | (2006.01) | |
| *G01N 21/88* | (2006.01) | |
| *G06T 7/40* | (2006.01) | |
| *B41F 33/00* | (2006.01) | |
| *G01N 21/89* | (2006.01) | |
| *H04N 5/33* | (2006.01) | |
| *G07D 7/12* | (2006.01) | |
| *A24C 5/34* | (2006.01) | |

(52) U.S. Cl.
CPC ............ *G01N 21/86* (2013.01); *B41F 33/0036* (2013.01); *G01N 21/88* (2013.01); *G01N 21/8806* (2013.01); *G01N 21/89* (2013.01); *G06T 7/408* (2013.01); *G07D 7/121* (2013.01); *H04N 5/33* (2013.01); *A24C 5/3412* (2013.01); *G06T 2207/10016* (2013.01)

(58) Field of Classification Search
CPC . G01N 21/88; G01N 21/8806; A24C 5/3412; G06T 7/408; G06T 2207/10016
See application file for complete search history.

(56) References Cited

U.S. PATENT DOCUMENTS

| 4,650,320 | A | 3/1987 | Chapman et al. | |
|---|---|---|---|---|
| 2006/0144266 | A1 | 7/2006 | Brown | |
| 2008/0259314 | A1 | 10/2008 | Kamijo | |
| 2010/0033708 | A1* | 2/2010 | Kriz ................................ | 356/51 |
| 2012/0176605 | A1* | 7/2012 | Stoeckli et al. ................. | 356/73 |
| 2013/0293726 | A1* | 11/2013 | Armstrong-Muntner et al. ............................ | 348/187 |

FOREIGN PATENT DOCUMENTS

| DE | 199 30 154 A1 | 1/2001 |
|---|---|---|
| JP | 2010-221410 A | 10/2010 |

OTHER PUBLICATIONS

Extended European Search Report dated May 22, 2015 issued in related application EP 13 17 6413.

* cited by examiner

*Primary Examiner* — Shawn An
(74) *Attorney, Agent, or Firm* — Birch, Stewart, Kolasch & Birch, LLP (57) ABSTRACT

An inspection apparatus for a sheet includes: white LED illuminators which irradiate a sheet of paper with light containing visible light: IR-LED illuminators which irradiate the sheet of paper with light containing infrared rays: two visible color cameras; one IR monochrome camera: an IR filter which eliminates the visible light in the light emitted from the white LED illuminators and the IR-LED illuminators and reflected off the sheet of paper, and makes only the infrared rays incident on the IR monochrome camera; and a control device which determines appropriateness of a pattern portion on the sheet of paper on the basis of the visible light made incident on the visible color cameras, and determines appropriateness of pattern portions on the sheet of paper on the basis of the infrared rays made incident on the IR monochrome camera.

3 Claims, 6 Drawing Sheets

INSPECTION APPARATUS FOR SHEET

TECHNICAL FIELD

The present invention relates to an inspection apparatus for a sheet including a pattern portion printed with an ordinary ink and a pattern portion printed with an ink containing an infrared component.

BACKGROUND ART

A conventional inspection apparatus of this type is disclosed in Patent Literature 1.

The inspection apparatus of Patent Literature 1 includes: a sheet holding device provided on an endless conveyor and configured to hold an end portion of a sheet; an arc-shaped track portion provided in part of a movement track of the sheet holding device in such a manner as to be directed inward of a loop formed by the movement track; multiple inspection apparatuses provided inside the loop of the arc-shaped track portion: and a guide member provided outside the loop of the arc-shaped track portion, in which the multiple inspection apparatuses inspect the sheet traveling along the arc-shaped track portion under the guidance of the guiding member.

In addition, the inspection apparatuses include: multiple imaging means such as CCD-line cameras; and multiple light sources such as LED illuminators and the like paired with the CCD-line cameras, as well as are radially arranged around the arc-shaped track portion.

CITATION LIST

Patent Literature

{Patent Literature 1} Japanese Patent Application Publication No. 2010-221410

SUMMARY OF INVENTION

Technical Problem

Meanwhile, in printing products such as bank notes and securities, some of patterns thereon are printed by use of an ink containing an infrared component in order to prevent counterfeiting. Accordingly, in the case of inspecting a pattern portion printed with the ink containing the infrared component and a pattern portion printed with an ordinary ink, it is necessary to form the arc-shaped track portion in part of the movement track of the sheet holding device as disclosed in Patent Literature 1, and moreover, to arrange the multiple inspection apparatuses (the imaging means, the light sources, and the like) for inspecting the pattern portions radially around the arc-shaped track portion or to newly arrange an inspection cylinder along the arc-shaped track portion.

As a consequence, a special space for installing the inspection devices is required. This leads to an increase in size of a printing press and an increase in equipment costs.

The present invention has been made to solve the aforementioned problem, and its object is to provide an inspection apparatus for a sheet, which is capable of inspecting a pattern portion printed with an ordinary ink and a pattern portion printed with an ink containing an infrared component while saving an installation space as well as costs.

Solution to Problem

An inspection apparatus for a sheet of the present invention for solving the above-mentioned problem is an inspection apparatus for a sheet including: a pattern portion printed with an ordinary ink; and a pattern portion printed with an ink containing an infrared component. The inspection apparatus is characterized by including: a white light source configured to irradiate the sheet with light containing visible light; an infrared light source configured to irradiate the sheet with light containing infrared rays; two visible light imaging means for imaging the sheet; one infrared imaging means for imaging the sheet, the infrared imaging means being located in a position which is out of the fields of view of the two visible light imaging means; an infrared filter configured to eliminate the visible light in the light which is emitted from the white light source and the infrared light source and reflected off the sheet, and to make only the infrared rays incident on the infrared imaging means; and a control device configured to determine appropriateness of the pattern portion printed with the ordinary ink on the sheet on the basis of the visible light emitted from the white light source and the infrared light source, reflected off the sheet, and made incident on the two visible light imaging means, and to determine appropriateness of the pattern portion printed with the ink containing the infrared component on the sheet on the basis of the infrared rays emitted from the white light source and the infrared light source, reflected off the sheet, and made incident on the one infrared imaging means.

In addition, the inspection apparatus for a sheet is characterized in that the infrared imaging means is installed between the two visible light imaging means disposed away from each other in a sheet width direction.

Furthermore, the inspection apparatus for a sheet is characterized in that the two visible light imaging means and the infrared imaging means are disposed in positions equidistant from an imaging plane of the sheet.

Advantageous Effects of Invention

According to the inspection apparatus for a sheet of the present invention, a pattern portion printed with an ordinary ink and a pattern portion printed with an ink containing an infrared component can be inspected at the same time and on the same imaging plane by compactly arranging the visible light imaging means and the infrared imaging means while utilizing the existing cylinder arrangement and the like. This makes it possible to save an installation space as well as costs for the inspection apparatus.

DESCRIPTION OF EMBODIMENT

An inspection apparatus for a sheet according to the present invention will be described below in detail by use of the drawings.

Embodiment

Figure 1:
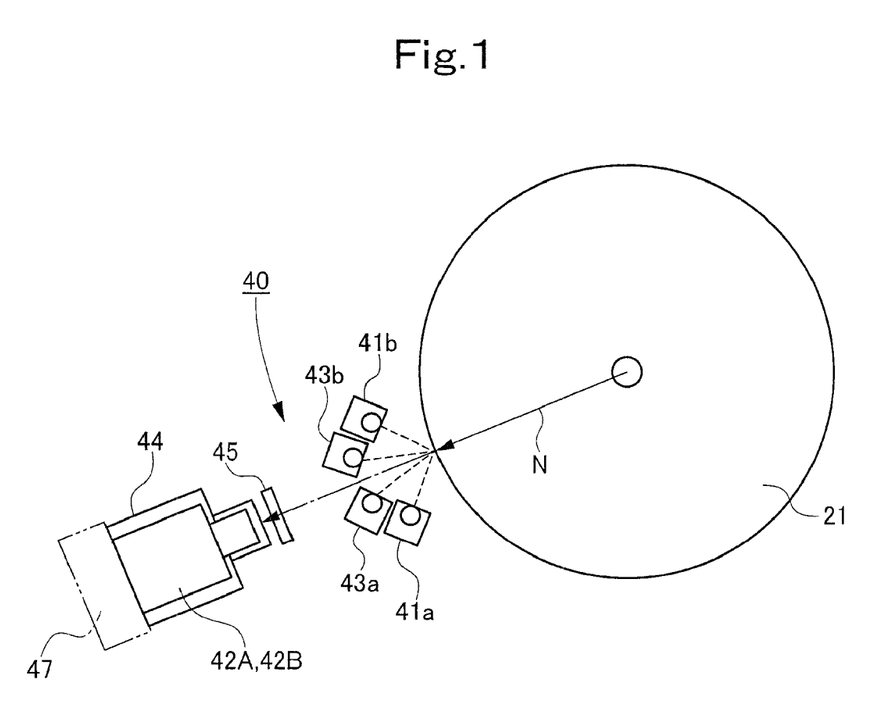
FIG. 1 is a side view of an inspection apparatus according to an embodiment of the present invention.
Figure 2:
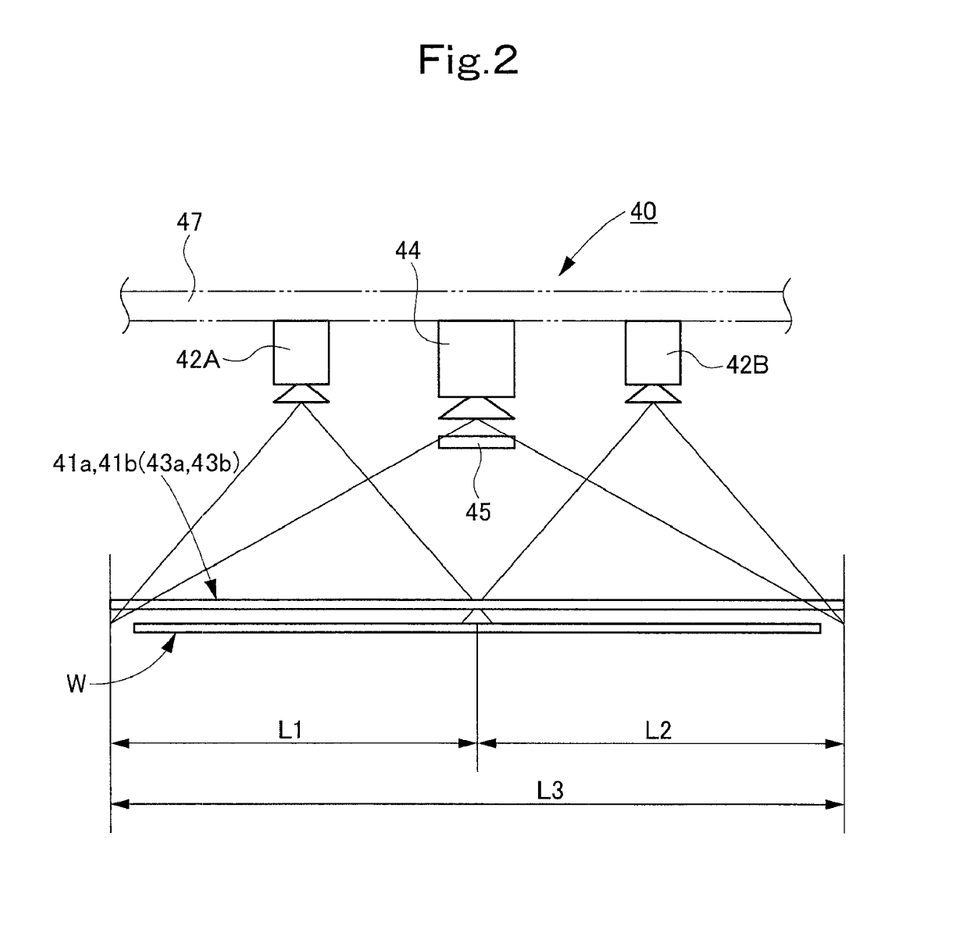
FIG. 2 is a front view of the inspection apparatus according to the embodiment of the present invention.
Figure 3:
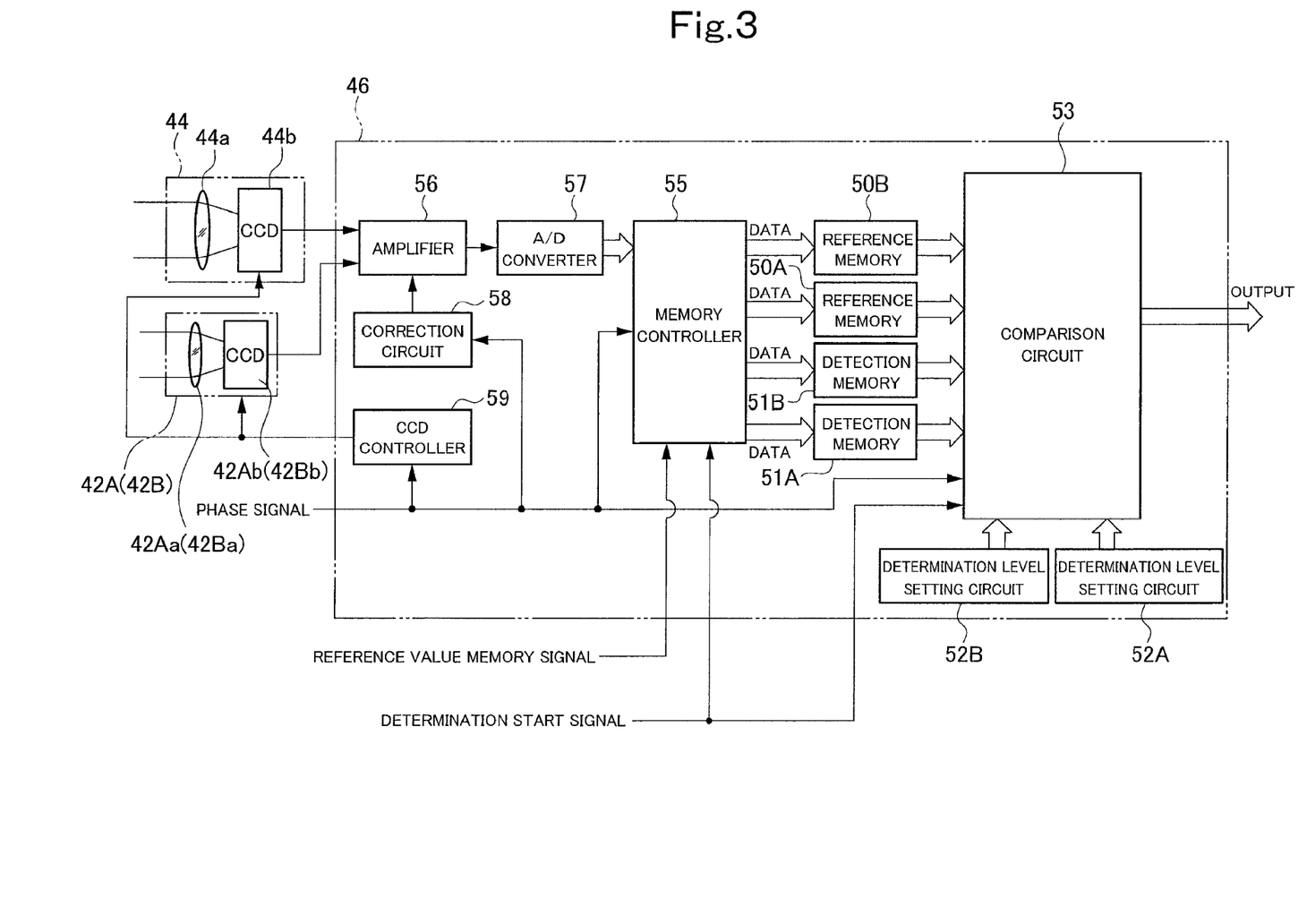
FIG. 3 is a control block diagram according to the embodiment of the present invention.
Figure 4:
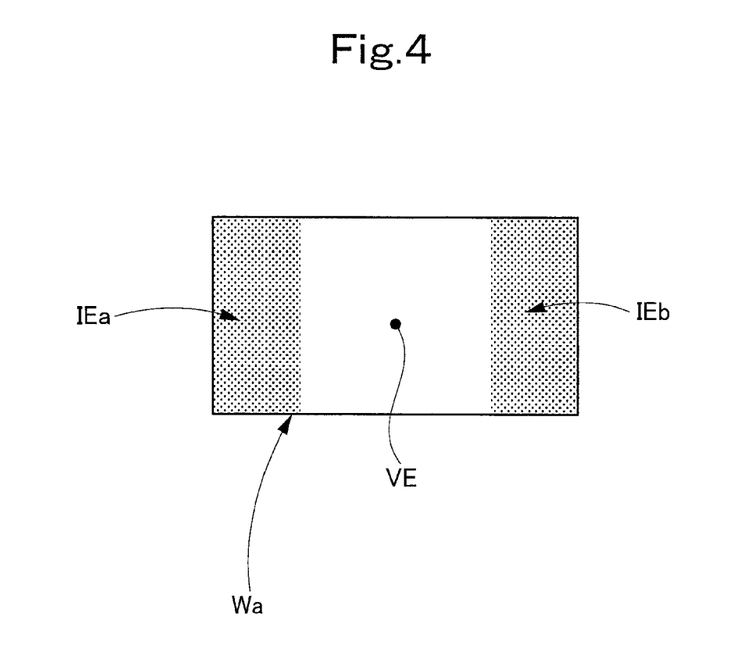
FIG. 4 is an explanatory view of patterns on paper.

FIG. 1 is a side view of an inspection apparatus according to an embodiment of the present invention, FIG. 2 is a front view of the inspection apparatus, and FIG. 3 is a control block diagram thereof. FIG. 4 is an explanatory view of patterns on paper. Further, FIG. 5 is a schematic configuration diagram of an intaglio printing press and FIG. 6 is an enlarged view of substantial part in FIG. 5.

Figure 5:
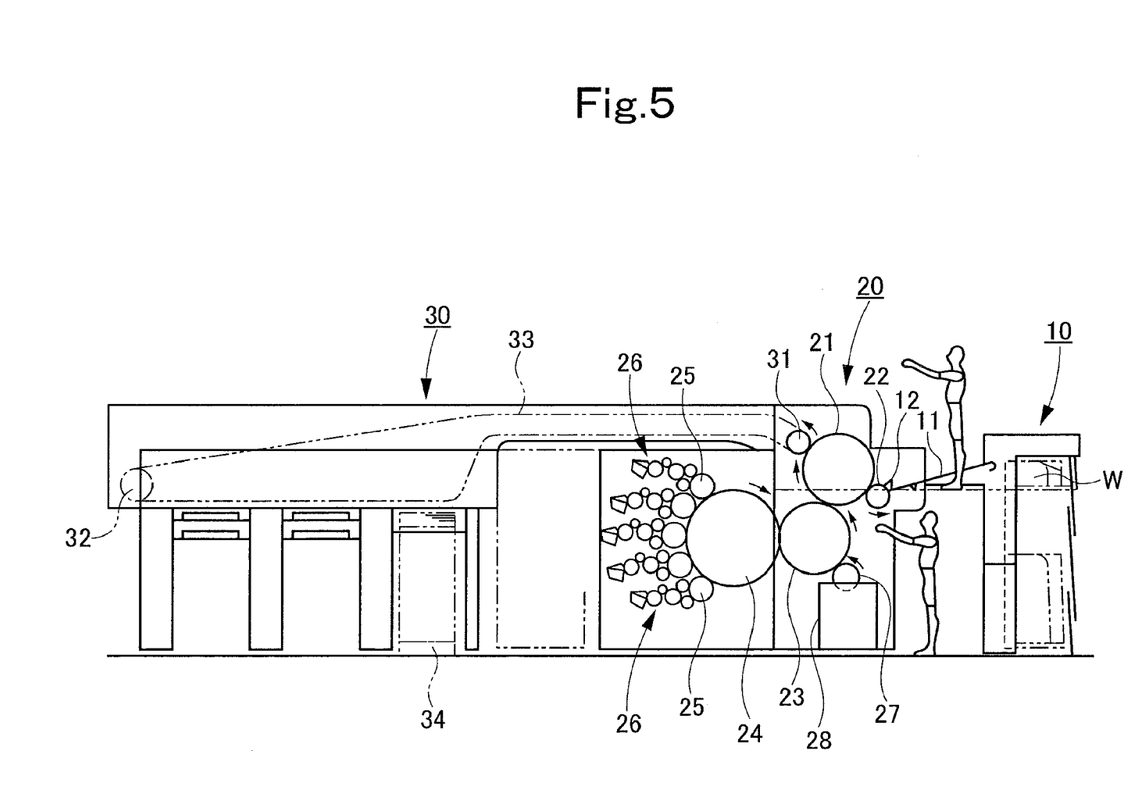
FIG. 5 is a schematic configuration diagram of an intaglio printing press to which the inspection apparatus according to the embodiment of the present invention is applied.
Figure 6:
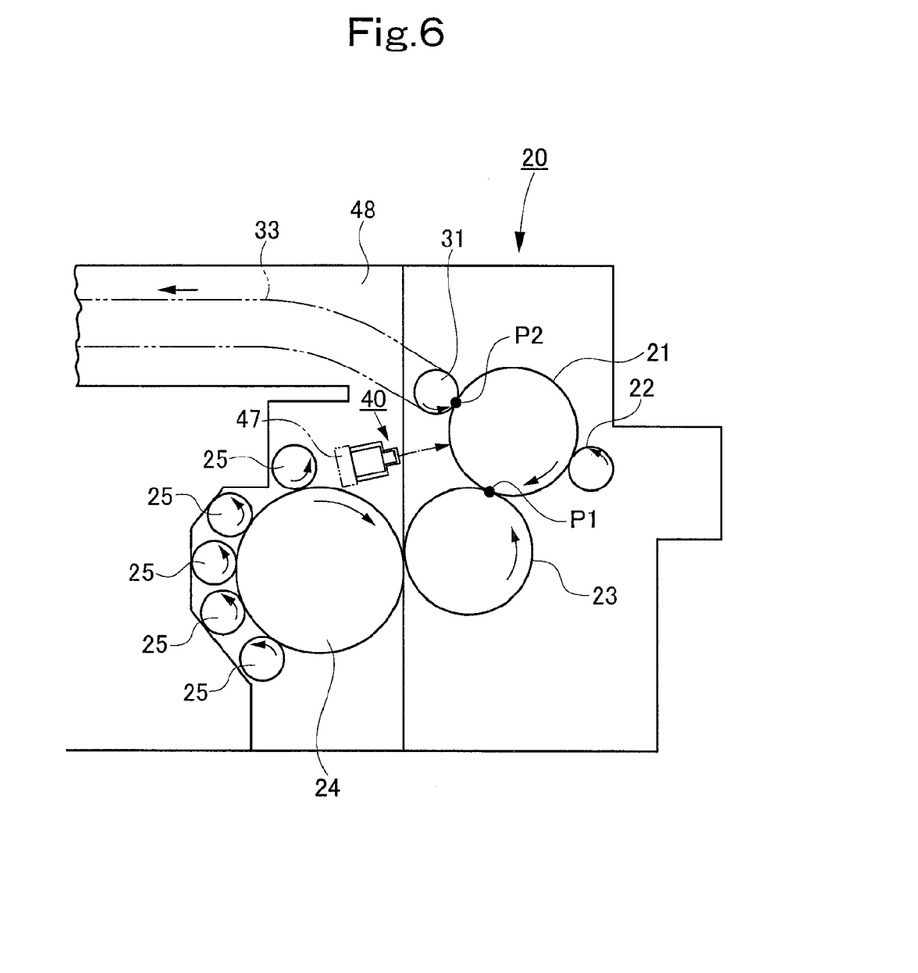
FIG. 6 is an enlarged view of substantial part in FIG. 5.

As shown in FIG. 5, an intaglio printing press, which serves as a printing press for a final stage in multiple printing steps of printing not only ordinary patterns but also numbers and seals, mainly includes a sheet feeder apparatus 10, a printing apparatus 20, and a sheet delivery apparatus 30.

A feedboard 11 is connected to a sheet feeder apparatus 10 on which sheets of paper (sheets) W are stacked. The feedboard 11 is configured to receive the sheets of paper W which are sent out one by one from the top of the stack by a sucker mechanism of the sheet feeder apparatus 10, and to align print registers on the sheets of paper W. Moreover, a swing arm shaft pregripper 12 configured to grip and swing each sheet of paper W on the feedboard 11 is disposed at a tip end portion of the feedboard 11.

In the printing apparatus 20, a so-called triple-size impression cylinder 21, on which three grippers are arranged at regular intervals in a circumferential direction to allow attachment of three rubber blankets, is connected to the swing arm shaft pregripper 12 via a transfer cylinder 22. A gripper similar to those on the impression cylinder 21 is provided on the transfer cylinder 22. The transfer cylinder 22 can receive the sheet of paper W transferred from the swing arm shaft pregripper 12 by use of the gripper on the transfer cylinder 22, and further transfer the sheet of paper W onto the corresponding gripper on the impression cylinder 21.

A so-called triple-size plate cylinder 23 to which three intaglio printing plates can be attached in a circumferential direction of the cylinder 23 is in contact with the impression cylinder 21. Moreover, a so-called quadruple-size ink collecting cylinder 24 to which four rubber blankets can be attached in a circumferential direction of the cylinder 24 is in contact with the intaglio printing plates on the plate cylinder 23.

Five of so-called single-size chablon rollers 25 each having a circumferential length corresponding to the length of each blanket on the impression cylinder 21 or each intaglio printing plate on the plate cylinder 23 are in contact with the ink collecting cylinder 24 while being arranged in a circumferential direction of the cylinder 24. In addition, inking devices 26 each being configured to supply an ink are in contact with the corresponding chablon rollers 25. Further, inks in mutually different colors are filled in the respective inking devices 26.

Meanwhile, a wiping roller 27 is in contact with any of the intaglio printing plates on the plate cylinder 23. The wiping roller 27 is dipped in a wiping tank 28 which stores a solvent.

A delivery cylinder 31 is provided in the sheet delivery apparatus 30. The delivery cylinder 31 is in contact with the impression cylinder 21. Meanwhile, delivery chains 33 are mounted between a pair of right and left sprockets (not shown) provided coaxially with the delivery cylinder 31 and a pair of right and left sprockets 32 disposed at an end portion of the sheet delivery apparatus 30 in such a way that each delivery chain 33 is wound around one of the sprockets (not shown) and around the corresponding one of the sprockets 32. The delivery chains 33 are provided with delivery grippers (not shown). In addition, multiple delivery pile boards 34 are disposed on a downstream side in a direction of travel of the delivery chains 33.

Accordingly, when the sheets of paper W are sent out one by one onto the feedboard 11 from the sheet feeder apparatus 10, each sheet of paper W is passed by the swing arm shaft pregripper 12 onto the transfer cylinder 22, and is then transferred from the gripper on the transfer cylinder 22 onto the gripper on the impression cylinder 21.

In the meantime, the inks in the inking devices 26 are transferred to the ink collecting cylinder 24 via the chablon rollers 25 and are then supplied onto surfaces of the intaglio printing plates on the plate cylinder 23. Subsequently, the inks supplied to the plate cylinder 23 are transferred onto the sheet of paper W held on the impression cylinder 21 at the time of its contact with the impression cylinder 21. Meanwhile, extra portions of the inks supplied to the plate cylinder 23 are removed by the wiping roller 27. The extra inks removed by the wiping roller 27 are cleaned away and removed from the wiping roller 27 using the solvent in the wiping tank 28.

The sheet of paper W printed by the transfer of the inks from the plate cylinder 23 as described above travels in response to rotation of the impression cylinder 21. Hence, the quality of the print on the sheet of paper W is inspected on a peripheral surface of the impression cylinder 21 by an inspection apparatus 40 to be described later.

Subsequently, the printed sheet of paper W is passed from the impression cylinder 21 onto the delivery cylinder 31 and is then gripped by the delivery grippers on the delivery chains 33 in the sheet delivery apparatus 30. Thereafter, the sheet of paper W gripped by the delivery grippers on the delivery chains 33 is conveyed by the delivery chains 33 and is then delivered onto one of the delivery pile boards 34.

In the embodiment, as shown in FIG. 6, the inspection apparatus 40 is disposed in a facing position to face the peripheral surface of the impression cylinder 21, which is located downstream of a position of contact (a printing position P1) of the impression cylinder 21 with the plate cylinder 23 in a rotating direction of the impression cylinder 21 and upstream of a position of contact (a sheet delivery position P2) of the impression cylinder 21 with the delivery cylinder 31 in the rotating direction of the impression cylinder 21. The inspection apparatus 40 is configured to inspect the quality of the print on the sheet of paper W which contains a pattern portion printed with ordinary inks (hereinafter referred to as visible inks) and a pattern portion printed with an ink containing an infrared component (hereinafter referred to as an IR ink).

As shown in FIG. 1 and FIG. 2, for the purpose of inspecting the visible inks, the inspection apparatus 40 includes: a pair of white LED illuminators (white light sources) 41a and 41b configured to irradiate the sheet of paper W with light containing the visible light; and two visible color cameras (visible light imaging means) 42A and 42B configured to take images of the sheet of paper W.

In addition, for the purpose of inspecting the IR ink, the inspection apparatus 40 includes: a pair of IR-LED illuminators (infrared light sources) 43a and 43b configured to irradiate the sheet of paper W with light containing infrared rays; one IR monochrome camera (infrared imaging means) 44 configured to take an image of the sheet of paper W; and an IR filter (infrared filter) 45 configured to eliminate light components having wavelengths not longer than the visible light from the light emitted from the white LED illuminators 41a and 41b as well as the IR-LED illuminators 43a and 43b and reflected by the sheet of paper W, and to make only the infrared rays incident on the IR monochrome camera 44.

There is also provided a control device 46 configured to determine appropriateness of the pattern portion printed with the visible inks and the pattern portion printed with the IR ink on the sheet of paper W on the basis of the visible light, which is emitted from the white LED illuminators 41a and 41b as well as the IR-LED illuminators 43a and 43b, reflected off the sheet of paper W, and made incident on the two visible color cameras 42A and 42B. The control device 46 is also configured to determine appropriateness of a shape of the pattern portion printed with the IR ink on the sheet of paper W on the basis of the infrared rays, which are emitted from the white LED illuminators 41a and 41b as well as the IR-LED illuminators 43a and 43b, reflected off the sheet of paper W, and made incident on the one IR monochrome camera 44.

The IR monochrome camera 44 is installed in a middle position between the two visible color cameras 42A and 42B disposed away from each other in a sheet width direction, the position being out of the fields of view of the two visible color cameras 42A and 42B. In FIG. 2, an inspection width of the visible color camera 42A is indicated as L1, an inspection width of the visible color camera 42B is indicated as L2, and an inspection width of the IR monochrome camera 44 is indicated as L3.

Meanwhile, the two visible color cameras 42A and 42B and the IR monochrome camera 44 are provided in a direction of a normal N to the centerline (the cylinder axis) of the impression cylinder 21, and are located in positions equidistant from an imaging plane of the sheet of paper W. Thus, the imaging plane of the sheet of paper W can be imaged in a perpendicular direction. Specifically, the three cameras 42A, 42B, and 44 are supported on a straight line parallel to the cylinder axis of the impression cylinder 21 by an apparatus frame 48 (see FIG. 6) via a support frame 47. Here, the white LED illuminators 41a and 41b as well as the IR-LED illuminators 43a and 43b are also supported by the apparatus frame 48 via support frames which are not shown.

Next, an optical and electrical configuration of the inspection apparatus 40 of the embodiment will be described by use of FIG. 3. The inspection apparatus 40 includes: the two visible color cameras 42A and 42B configured to image the pattern portion printed with the visible inks on the sheet of paper W; the IR monochrome camera 44 configured to image the pattern portion printed with the IR ink on the sheet of paper W; and the control device 46 configured to inspect the printing quality of the patterns printed on the sheet of paper W on the basis of imaging outputs from the cameras 42A, 42B, and 44. Each of the cameras 42A, 42B, and 44 includes: an optical system having a lens 42Aa, 42Ba or 44a; and a CCD (charge coupled device) 42Ab, 42Bb or 44b configured to convert an image formed by the corresponding optical system into electric signals.

The control device 46 includes: reference memories 50A (for the IR monochrome camera) and 50B (for the visible color cameras) configured to store reference image signals; detection memories 51A (for the IR monochrome camera) and 51B (for the visible color cameras) configured to store detection image signals; a memory controller 55 configured to control writing and reading of the signals in and out of the reference memories 50A and 50B as well as the detection memories 51A and 51B; determination level setting circuits 52A (for the IR monochrome camera) and 52B (for the visible color cameras) respectively configured to set an allowable level difference between a pair of signals read out of the reference memory 50A and the detection memory 51A and an allowable level difference between a pair of signals read out of the reference memory 50B and the detection memory 513; a comparison circuit 53 configured to compare the pairs of signals in consideration of the allowable level differences set by the determination level setting circuits 52A and 52B; an amplifier 56 configured to amplify outputs from the CCDs 42Ab, 42Bb, and 44b; an A/D converter 57 configured to perform analog-to-digital conversion of outputs from the amplifier 56 and to output the converted outputs to the memory controller 55; a correction circuit 58 configured to adjust gains of the amplifier 56; and a CCD controller 59 configured to control the CCDs 42Ab, 42Bb, and 44b.

At the start of a printing job, the reference memories 50A and 50B store reference image data which are read from the pattern portion printed normally on the sheet of paper W with the visible inks and the pattern portion printed normally on the sheet of paper W with the IR ink. Here, each of the reference memories 50A and 50B stores different image data depending on the printing job. The detection memories 51A and 51B store detection image data read from the sheet of paper W as an object of inspection.

The memory controller 55 controls writing and reading of the data in and out of the reference memories 50A and 50B as well as the detection memories 51A and 51B. The determination level setting circuits 52A (for the IR monochrome camera) and 52B (for the visible color cameras) preset the allowable level differences between reference image data read out of the reference memories 50A and 50B and the detection image data read out of the detection memories 51A and 51B.

If any of the level differences between the reference image data and the detection image data read by the memory controller 55 is equal to or above the corresponding allowable level difference set by the determination level setting circuit 52A or 52B, the comparison circuit 53 outputs a signal indicating that the corresponding pattern portion has defective quality. Specifically, pieces of the reference image data and pieces of the detection image data corresponding to pixels of the CCDs 42Ab, 42Bb, and 44b are compared one by one, whereby the levels of the two types of data corresponding to each of the pixels are compared. A defective signal is outputted if any one of the level differences is equal to or above the corresponding allowable level difference.

To be more precise, the comparison circuit 53 performs a first comparison operation to sequentially compare the pieces of the reference image data read out of the reference memories 50A and 50B with the pieces of the detection image data read out of the detection memories 51A and 51B on the pixel basis. Next, the comparison circuit 53 performs a second comparison operation to compare the level differences between the pairs of signals obtained by the first comparison operation with the allowable level differences outputted from the determination level setting circuits 52A and 52B. If the level differences of the pairs of signals are greater than the allowable level differences as a result of the second comparison operation, the comparison circuit 53 outputs a defective signal indicating that the pattern portion printed with the visible inks and the pattern portion printed with the IR ink on the sheet of paper W, as the object of inspection, are defective.

The correction circuit 58 adjusts the gains of the amplifier 56 in accordance with a rotating speed of the impression cylinder 21. Specifically, even when the same amount of light is incident on the cameras 42A, 42B, and 44, output levels of the CCDs 42Ab, 42Bb, and 44b become smaller as the rotating speed of the impression cylinder 21 is faster. For this reason, the influence of the rotating speed is eliminated by the correction circuit 58. A phase signal of the impression cylinder 21 is supplied to the memory controller 55, the comparison circuit 53, the correction circuit 58, and the CCD controller 59. A reference value memory signal is supplied to the memory controller 55. A determination start signal is supplied to the memory controller 55 and the comparison circuit 53.

The phase signal is originated from an output signal of a rotary encoder (not shown) configured to detect a rotational phase of the impression cylinder 21. The phase signal includes: a reference pulse which rises once each turn of the impression cylinder 21; and a clock pulse which rises for each predetermined number of turns of the impression cylinder 21. The reference value memory signal is a signal used for causing the reference image data to be read into the reference memories 50A and 50B through the memory controller 55, and is supplied by an operation of a reference value memory switch (not shown) by an operator. The determination start signal is a signal instructing the start of the comparison operation between the reference image data and the detection image data, and is supplied by an operation of a determination start switch (not shown) by the operator.

In the above-described configuration, the reference image data corresponding to the pattern portion printed normally on the sheet of paper W with the visible inks and the pattern portion printed normally on the sheet of paper W with the IR ink is acquired as a pre-process of a quality inspection step. First, the operator confirms a condition of the print on the sheet of paper W in the course of test printing using the sheet of paper W. When the condition of the print is confirmed to be fine, the supply of the reference value memory signal to the control device 46 is started by the operation of the reference value memory switch. Once a reference signal indicating a reference position of the impression cylinder 21 is outputted from the rotary encoder, the acquisition of the reference image data from the sheet of paper W held and conveyed by the impression cylinder 21 is started, and the acquired data are stored in the reference memories 50A and 50B.

After the reference image data on the sheet of paper W held and conveyed by the impression cylinder 21 are stored in the reference memories 50A and 50B, determination processing is started by supplying the determination start signal. In the determination processing, first of all, in response to the rotation of the impression cylinder 21, detection image data on the sheet of paper W held and conveyed by the impression cylinder 21 are read into the detection memories 51A and 51B as in the case of reading the reference image data. Next, the detection image data read in the determination processing are compared with the reference image data stored in advance. Then, appropriateness of the pattern portion printed with the visible inks on the sheet of paper W and appropriateness of the pattern portion printed with the IR ink on the sheet of paper are respectively determined based on whether or not the level values of the two types of data fall within the corresponding allowable level differences.

For example, FIG. 4 shows an image taken with the IR monochrome camera 44. Here, in each of numerous pieces (such as bank notes and securities) Wa on the sheet of paper W as the object of inspection, a pattern portion VE printed with the visible inks entirely appears white because the visible light emitted from the while LED illuminators 41a and 41b as well as the IR-LED illuminators 43a and 43b onto the imaging plane of the pattern portion VE and reflected off the imaging plane thereof is completely eliminated by the IR filter 45 whereas only the unfiltered infrared rays reflected off the imaging plane thereof are made incident.

In the meantime, pattern portions IEa and IEb printed with the IR ink, which are located on two sides of the pattern portion VE printed with the visible inks, appear vivid black because the infrared rays emitted from the while LED illuminators 41a and 41b as well as the IR-LED illuminators 43a and 43b onto the imaging plane of the pattern portions IEa and IEb and reflected off the imaging plane while being absorbed by the IR ink are made incident through the IR filter 45.

As a consequence, it is possible to inspect detailed shapes of the pattern portions IEa and IEb printed with the IR ink. On the other hand, the visible color cameras 42A and 42B take images of the pattern portion VE printed with the visible inks as well as the pattern portions IEa and IEb printed with the IR ink in the same colors as those are viewed by the human eye. Thus, it is possible to inspect the portion VE as well as the portions IEa and IEb in detail.

As described above, the pattern portion VE printed with the visible inks as well as the pattern portions IEa and IEb printed with the IR ink can be inspected at the same time and on the same imaging plane since the visible light and the infrared rays have mutually different light wavelengths.

Thus, the embodiment enables the inspection of the pattern portion VE printed with the visible inks as well as the pattern portions IEa and IEb printed with the IR ink at the same time and on the same imaging plane of the existing impression cylinder 21 without providing a dedicated inspection cylinder. Accordingly, it is possible to avoid an increase in size of a printing press by reducing the space for the inspection apparatus 40, and to reduce equipment costs by reducing the number of components and the like.

Needless to say, the present invention is not limited only to the foregoing embodiment and various changes including changes in cylinder arrangements, ink colors, and the like are possible without departing from the gist of the present invention.

INDUSTRIAL APPLICABILITY

An inspection apparatus for a sheet according to the present invention is applicable to a special printing press for printing bank notes, securities, and the like, where quality management is important.

REFERENCE SIGNS LIST

10 SHEET FEEDER APPARATUS
11 FEEDBOARD
12 SWING ARM SHAFT PREGRIPPER
20 PRINTING APPARATUS
21 IMPRESSION CYLINDER
22 TRANSFER CYLINDER
23 PLATE CYLINDER
24 INK COLLECTING CYLINDER
25 CHABLON ROLLER
26 INKING DEVICE
27 WIPING ROLLER
28 WIPING TANK
30 SHEET DELIVERY APPARATUS
31 DELIVERY CYLINDER
32 SPROCKET
33 DELIVERY CHAIN
34 DELIVERY PILE BOARD
40 INSPECTION APPARATUS
41a, 41b WHITE LED ILLUMINATOR (WHITE LIGHT SOURCE)
42A, 42B VISIBLE COLOR CAMERA (VISIBLE LIGHT IMAGING MEANS)
42Aa, 42Ba LENS
42Ab, 42Bb CCD (CHARGE COUPLED DEVICE)
43a, 43b IR-LED ILLUMINATOR (INFRARED LIGHT SOURCE)
44 IR MONOCHROME CAMERA (INFRARED IMAGING MEANS)
44a LENS
44b CCD (CHARGE COUPLED DEVICE)
45 IR FILTER (INFRARED FILTER)
46 CONTROL DEVICE
50A REFERENCE MEMORY (FOR IR MONOCHROME CAMERA)

50B REFERENCE MEMORY (FOR VISIBLE COLOR CAMERAS)
51A DETECTION MEMORY (FOR IR MONOCHROME CAMERA)
51B DETECTION MEMORY (FOR VISIBLE COLOR CAMERAS)
52A DETERMINATION LEVEL SETTING CIRCUIT (FOR IR MONOCHROME CAMERA)
52B DETERMINATION LEVEL SETTING CIRCUIT (FOR VISIBLE COLOR CAMERAS)
53 COMPARISON CIRCUIT
55 MEMORY CONTROLLER
56 AMPLIFIER
57 A/D CONVERTER
58 CORRECTION CIRCUIT
59 CCD CONTROLLER
W SHEET OF PAPER (SHEET)
Wa PIECE OF PAPER (BANK NOTE, SECURITY, etc.)
P1 PRINTING POSITION
P2 SHEET DELIVERY POSITION
VE PATTERN PORTION PRINTED WITH VISIBLE INKS
IEb PATTERN PORTION PRINTED WITH IR INK
L1 INSPECTION WIDTH OF VISIBLE COLOR CAMERA 42A
L2 INSPECTION WIDTH OF VISIBLE COLOR CAMERA 42B
L3 INSPECTION WIDTH OF IR MONOCHROME CAMERA 44

The invention claimed is:

1. An inspection apparatus for a sheet including a pattern portion printed with an ordinary ink and a pattern portion printed with an ink containing an infrared component, comprising:

a white light source configured to irradiate the sheet with light containing visible light;

an infrared light source configured to irradiate the sheet with light containing infrared rays;

two visible light imaging means for imaging the sheet;

one infrared imaging means for imaging the sheet, the infrared imaging means being located in a position which is out of fields of view of the two visible light imaging means;

an infrared filter configured to eliminate the visible light in the light emitted from the white light source and the infrared light source and reflected off the sheet, and to make only the infrared rays incident on the infrared imaging means; and a control device configured to determine appropriateness of the pattern portion printed with the ordinary ink on the sheet on the basis of the visible light emitted from the white light source and the infrared light source, reflected off the sheet, and made incident on the two visible light imaging means, and to determine appropriateness of the pattern portion printed with the ink containing the infrared component on the sheet on the basis of the infrared rays emitted from the white light source and the infrared light source, reflected off the sheet, and made incident on the one infrared imaging means.

2. The inspection apparatus for a sheet according to claim 1, wherein the infrared imaging means is installed between the two visible light imaging means disposed away from each other in a sheet width direction.

3. The inspection apparatus for a sheet according to claim 1, wherein the two visible light imaging means and the infrared imaging means are disposed in positions equidistant from an imaging plane of the sheet.

* * * * *